(12) United States Patent
Growcock et al.

(10) Patent No.: US 8,994,389 B2
(45) Date of Patent: Mar. 31, 2015

(54) AUTOMATED ELECTRICAL STABILITY METER

(75) Inventors: Frederick B. Growcock, Houston, TX (US); Marian Baranowski, Houston, TX (US); Donovan Balli, Houston, TX (US)

(73) Assignee: M-I L.L.C., Houston, TX (US)

( * ) Notice: Subject to any disclaimer, the term of this patent is extended or adjusted under 35 U.S.C. 154(b) by 169 days.

(21) Appl. No.: 12/741,051

(22) PCT Filed: Nov. 7, 2008

(86) PCT No.: PCT/US2008/082809
§ 371 (c)(1),
(2), (4) Date: May 3, 2010

(87) PCT Pub. No.: WO2009/062041
PCT Pub. Date: May 14, 2009

(65) Prior Publication Data
US 2010/0283492 A1 Nov. 11, 2010

Related U.S. Application Data

(60) Provisional application No. 60/986,831, filed on Nov. 9, 2007.

(51) Int. Cl.
*G01R 27/08* (2006.01)
*G01N 33/28* (2006.01)

(52) U.S. Cl.
CPC .................................. *G01N 33/2823* (2013.01)
USPC ........................................ 324/724; 324/722

(58) Field of Classification Search
USPC ......................................................... 324/724
See application file for complete search history.

(56) References Cited

U.S. PATENT DOCUMENTS

| | | | |
|---|---|---|---|
| 4,023,096 A | 5/1977 | Schmidt | |
| 4,724,589 A * | 2/1988 | Walker | ........................ 29/81.01 |
| 4,734,580 A | 3/1988 | Rodrigo et al. | |
| 6,801,039 B2 | 10/2004 | Fabris et al. | |
| 6,906,535 B2 | 6/2005 | Murphy, Jr. et al. | |
| 2007/0151762 A1* | 7/2007 | Reitsma | ......................... 175/40 |
| 2007/0247328 A1* | 10/2007 | Petrovic et al. | ............ 340/853.7 |
| 2010/0256914 A1* | 10/2010 | Hutin et al. | ......................... 702/9 |

OTHER PUBLICATIONS

Fann 23D Electrical Stability Tester (EST) specifications, Fann Instrument Company, 2007, p. 1-2, http://eurosul.com/brochures/Electrical_Stability_Tester_EST.pdf.*
Lee, PCT/US/2006/060919, WO 2007/073517, Jun. 28, 2007, p. 1-15.*
Examination Report issued in corresponding Saudi Arabian Application No. 08 29 0716, dated Sep. 13, 2011 and English explanation thereof (10 pages).

(Continued)

*Primary Examiner* — Thomas F Valone

(57) ABSTRACT

A method for automatically measuring a property of a fluid associated with a drilling application, including obtaining a sample of the fluid, wherein the sample of the fluid is obtained by directing the fluid through an electrode probe assembly comprising an electrode probe and depositing the fluid in a probe gap between electrodes of the electrode probe, ramping up a voltage applied to the electrodes of the electrode probe until a threshold current is obtained, recording the breakdown voltage at the threshold current value, and using the breakdown voltage to compute the property of the sample of the fluid.

16 Claims, 2 Drawing Sheets

(56) References Cited

OTHER PUBLICATIONS

International Search Report from PCT/US2008/082809 dated Jun. 19, 2009 (3 pages).
Written Opinion from PCT/US2008/082809 dated Jun. 19, 2009 (4 pages).
Examiner's Report issued in corresponding Canadian Application No. 2,704,677, dated Mar. 8, 2012 (3 pages).
Office Action issued in corresponding Mexican Application No. MX/a/2010/005058 and English Reporting thereof dated Jul. 30, 2013 (9 pages).
Office Action issued in corresponding European Application No. 08848125.4 dated Aug. 22, 2013 (4 pages).
Office Action issued in corresponding Eurasian Application No. 201070593; Dated May 25, 2012 (2 pages).
Supplementary Search Report and Opinion issued in corresponding European Application No. 08 848 125.4; Dated Jul. 31, 2012 (6 pages).
Growcock F B et al: "Electrical stability, emulsion stability, and wettability of invert oil-based muds", SPE Drilling and Completion, The Society, Richardson, TX, US, vol. 9, No. 1, Mar. 1, 1994, pp. 39-46, XP009122283, ISN: 1064-6671, DOI: 10.2118/20435-PA.
Ali A et al; "Investigation of the electrical stability test for oil muds", Proceedings SPE/IADC Drilling Conference, XX, XX, No. 16077, Mar. 15, 1987, pp. 227-241, XP002261884.
Office Action issued in corresponding European Application No. 08848125.4; Dated Apr. 4, 2013 (5 pages).
Official Action issued in corresponding Eurasian Application No. 201070593; Dated Nov. 9, 2012 (4 pages).
Official Action issued in corresponding Eurasian Application No. 201070593; Dated Apr. 5, 2013 (5 pages).
Official Action issued in corresponding Eurasian Application No. 201070593/31 with English translation dated Nov. 5, 2013 (3 pages).
Official Action issued in corresponding Eurasian Application No. 201070593/31 with English translation dated Jun. 5, 2014 (3 pages).
Office Action issued in corresponding European Application No. 08848125.4 dated Jan. 28, 2014 (3 pages).

* cited by examiner

AUTOMATED ELECTRICAL STABILITY METER

BACKGROUND OF INVENTION

1. Field of the Invention

Embodiments disclosed herein relate to an automated meter to measure the electrical stability of invert emulsion oil-based or synthetic-based fluids.

2. Background Art

When drilling oil and/or gas wells, oil-based drilling fluids are often used to cool the drill bit, remove rock chips, and control subsurface fluids. Various properties of this fluid can be measured to compute useful results. For example, the electrical stability of drilling fluid is a property that is typically measured using an electrical stability (ES) test. The ES test is typically a manual test that is performed by a mud engineer or an equivalent technician. Conventionally, when performing an ES test, a probe that includes circular flat electrodes of diameter 1/8 inch, spaced 1/16 inch between faces, is inserted into the drilling fluid. Drilling fluid, which contains non-aqueous fluid, water (or other polar liquid), clays, and other materials, fills the gap between the two electrodes of the test probe. Wires run from the probe to a signal generator and measurement meter, which ramps the voltage between the electrodes until components of the fluid align to form a short-circuiting bridge. When the short circuit occurs, the current between the electrodes immediately spikes. Specifically, an AC voltage of 340 Hz is ramped at 150 V s$^{-1}$ until a peak current (approximately 61 µA) occurs. At this stage, the peak voltage, known as the breakdown voltage ($V_{BD}$) is captured by the meter. 61 µA is the current at which the breakdown voltage occurs for the above-described geometry of the probe. The breakdown voltage is the voltage at which the drilling fluid's electrical properties become electric field-dependent and is the voltage at which the electrical conductivity of the drilling fluid becomes non-ohmic. Thus, the breakdown voltage is related to the emulsion stability and is then used to compute the emulsion stability and other properties of the drilling fluid.

Typically, to measure the electrical stability of drilling fluid using the above manual probe method, the drilling fluid and associated fluid is kept static, as movement and shifts in the fluids of the drilling fluid may cause the measurements taken by the electrodes and recorded by the meter to be skewed. In addition, when using the manual probe method described above, the electrodes and the gap between electrodes of the probe are manually cleaned after each measurement sampling.

Accordingly, there exists a need for an automated method for measuring the electrical stability of drilling fluid. Additionally, there exists a need for improved methods for sampling drilling fluid for appropriate measurements and cleaning of the electrodes of the probe used to measure the breakdown voltage of the drilling fluid.

SUMMARY OF INVENTION

In general, in one aspect, the invention relates to a method for automatically measuring a property of a fluid associated with a drilling application, comprising obtaining a sample of the fluid, wherein the sample of the fluid is obtained by directing the fluid through an electrode probe assembly comprising an electrode probe and depositing the fluid in a probe gap between electrodes of the electrode probe, ramping up a voltage applied to the electrodes of the electrode probe until a threshold current is obtained, recording the breakdown voltage at the threshold current value, and using the breakdown voltage to compute the property of the sample of fluid.

In general, in one aspect, the invention relates to An automated electrical stability meter for automatically measuring the electrical stability of a sample of fluid, comprising an electronic control module configured to send a signal to obtain a sample of the fluid, a probe assembly, operatively connected to the electronic control module, comprising an electrode probe, wherein the electrode probe comprises a probe gap, and wherein the sample of fluid is pumped through the probe assembly and fills the probe gap, wherein a voltage is ramped to obtain a breakdown voltage measurement that occurs at a threshold current value, and wherein the breakdown voltage measurement is used to automatically measure a property of the sample of the fluid.

Other aspects and advantages of the invention will be apparent from the following description and the appended claims.

DETAILED DESCRIPTION

Figure 1:
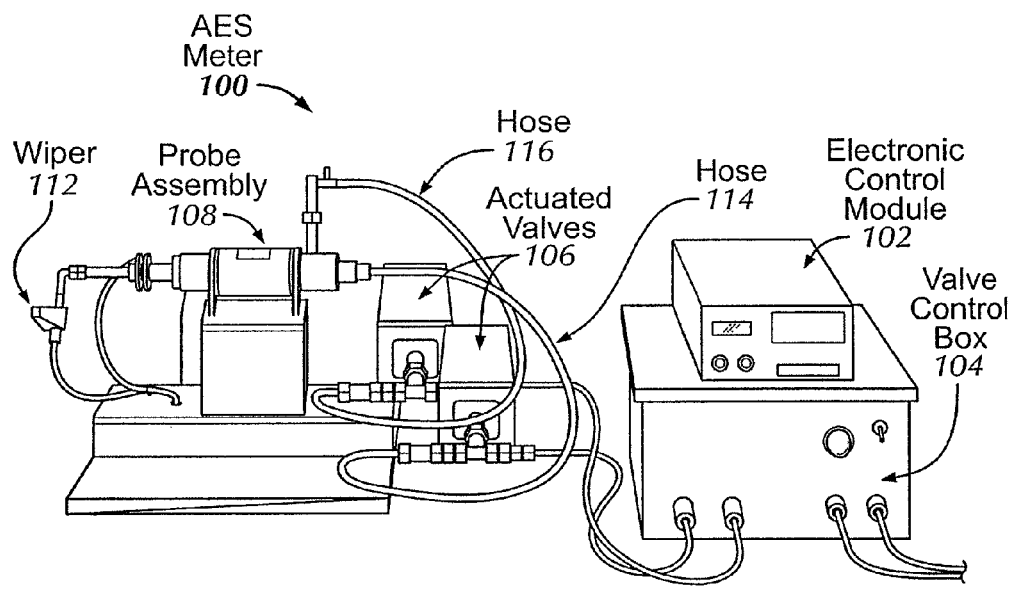
FIG. 1 shows an automated electrical stability meter in accordance with embodiments disclosed herein.

Specific embodiments of the invention will now be described in detail with reference to the accompanying figures. Like elements in the various figures are denoted by like reference numerals for consistency.

In the following detailed description of embodiments of the present disclosure, numerous specific details are set forth in order to provide a more thorough understanding of the invention. However, it will be apparent to one of ordinary skill in the art that the invention may be practiced without these specific details. In other instances, well-known features have not been described in detail to avoid unnecessarily complicating the description.

In one aspect, embodiments disclosed herein relate to a method and apparatus for automating the measurement of properties of invert emulsion oil-based or synthetic-based fluids (i.e., drilling fluids and/or completion fluids). Although the disclosure herein may reference drilling fluid, one of ordinary skill in the art will appreciate that other types of fluids (e.g., completion fluids) may also be tested with the system disclosed herein.

FIG. 1 shows an automated electrical stability (AES) meter (100) in accordance with one or more embodiments of the invention. The AES meter (100) includes an electronic control module (ECM) (102), a valve control box (104), actuated valves (106), a probe assembly (108), and a wiper (112). Each of the aforementioned components of the AES meter (100) is described in detail below.

In one or more embodiments of the invention, the AES meter (100) operates in two modes: automatic mode and manual mode. In automatic mode, the ECM (102) drives the actuated valves (106) and the probe assembly (108) by sending periodic signals initializing each measurement reading. In manual mode, the timing of readings is controlled manually; thus, a signal from a user indicating that a reading should be made is received by the ECM. Manual mode may also be used to check the meter calibration. The ECM (102) is configured to control the timing between measurement readings/data acquisition. Those skilled in the art will appreciate that the frequency of measurement readings may be determined by factors other than timing. For example, drilling fluid may be sampled and measured based on the quantity of drilling fluid that is driven through the probe assembly. Alternatively, drilling fluid may be sampled and measured on-demand.

In one or more embodiments, configuration files stored on a USB flash drive (not shown) or other type of computer readable medium or storage device are provided to the ECM (102) via a USB connector (not shown). Those skilled in the art will appreciate that other types of connectors and storage devices may also be employed. For example, an SD card and corresponding SD connector may be used to store and load configuration files. Alternatively, a hard drive, floppy disk drive, internal memory, or a CD may also be used. The configuration files include probe waveform definitions, calibration data, and automated and manual process definitions for the ECM (102). The standard API electrical stability test specifies a 340 Hz sinusoidal AC signal that ramps from 0-2000 volts at 150 volts per second. The procedure (i.e., software) stored in a configuration file is used to drive the actuated valves (106) and to determine when to drive a particular waveform signal to the probe assembly (108). In one or more embodiments, the waveform(s) are stored as separate files and may not be part of the configuration file. The API standard ES reading is the peak voltage at which the current reaches 61 μA. However, the configuration file may also provide the ECM with signals that are based on a non-linear voltage ramp and/or other types of ramp rates. Those skilled in the art will appreciate that the specifications of the electrical stability test may be changed by programming different waveforms onto the configured file that is fed to the ECM (102). Thus, the threshold current may be a value higher or lower than 61 μA.

Continuing with FIG. 1, the valve control box (104) is operatively connected to the ECM (102) and includes a power supply and solid-state relays to drive (i.e., open and close) the valve actuators (106). Terminal blocks (not shown) allow for connection of the valve control box (104) to the power supply and the actuated valves (106). The actuated valves (106) include ½ inch tubing connections for drilling fluid and ½ inch conduit ports for the electrical cabling. One of ordinary skill in the art will appreciate that other sized tubing connections and ports may be used without departing from the scope of embodiments disclosed herein. The ports are suitable for use with rigid conduit or watertight cord grips. The conduit ports associated with the valve actuators (106) connect to the valve control box (104).

Figure 2:
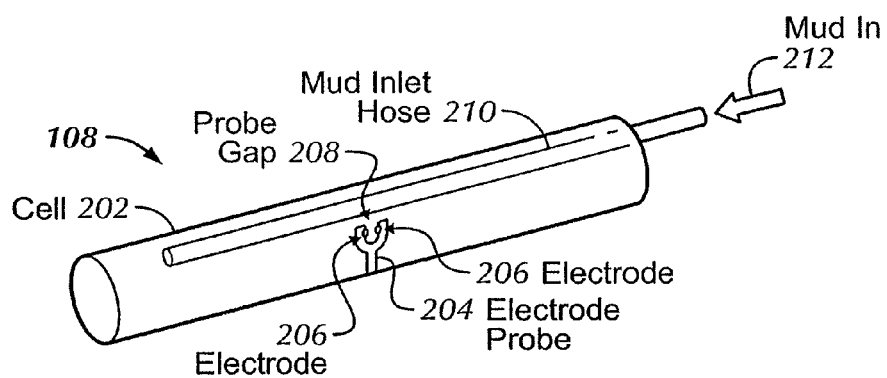
FIG. 2 shows a probe assembly in accordance with embodiments disclosed herein.

The ECM (102) is also operatively connected to the probe assembly (108). A more detailed view of the probe assembly (108) is shown in FIG. 2. In one or more embodiments disclosed herein, the probe assembly (108) includes a cell (202) with an electrode probe (204) for measuring the electrical stability and other properties of the drilling fluid. The electrode probe (204) is a fork-shaped probe with two electrodes (206) on each tong-like piece. Between the two electrodes is a probe gap (208). The electrode probe is placed within the sample cell (202) that is part of a by-pass system to a flow-line. Further, the cell (202) includes a hose/tube (210) that directs (i.e., conveys) drilling fluid from one end of the cell (202) to the other end of the cell (202), which ensures that a portion of the drilling fluid is deposited in the probe gap (208). More specifically, in one or more embodiments disclosed herein, the flow of the drilling fluid is diverted to the by-pass system (i.e., the probe assembly) using a low-flow-rate motorized pump (not shown). The drilling fluid is captured from the oil rig and pumped into the cell (202) (or a sample chamber) of the probe assembly (108) via two hoses (114, 116) that are also a part of the by-pass system. In one or more embodiments disclosed herein, the hoses (114, 116) may be stainless steel-sheathed flexible hoses that are attached to the wiper and probe assembly (108). In FIG. 1, a straight fitting hose acts as the mud inlet (114) and an elbow fitted hose acts as the mud outlet (116). In FIG. 2, the mud inlet (212) is shown. The hoses (114, 116) are attached to the actuated valves (106) to ensure that mud flows through the probe assembly (108) during the drilling fluid sampling phase of the AES measurement.

Returning to FIG. 1, in one or more embodiments disclosed herein, the wiper (112) is a separate piece of hardware operatively connected to the probe assembly and used to clean the probe gap and the probe electrodes between intervals in which drilling fluid is being pumped through the probe assembly (108). More specifically, the wiper (112) is an actuated squeegee that cleans the electrodes by being driven into the probe gap, removing the drilling fluid in the probe gap, and then being driven out of the probe gap. In one or more embodiments, the actuated wiper (112) may be made out of steel or sheet metal. The ECM is configured to drive the wiper (112) and determines when cleaning of the probe electrodes is performed.

Those skilled in the art will appreciate that the AES meter may employ other mechanisms for cleaning the electrodes associated with the probe, and is not limited to the above-described wiper. For example, the AES meter may employ conventional ultrasound techniques, which result in removal of the drilling fluid in between the electrodes. For example, there may be separate jets installed beside the electrode probe, which may be used to blast any deposit off of the electrodes and remove previously tested drilling fluid from the probe gap. More specifically, high-speed jetting of fresh fluid onto the surfaces of the electrodes and in the probe gap may be used to clean the electrode probe between samplings. Alternatively, the probe itself may be oscillated at high speeds to shake off the mud that may be deposited on and around the electrodes of the probe. Further, combinations of the above-mentioned cleansing methods may also be employed to clean the electrode probe.

The AES meter (100) is configured to automatically take a sample of the drilling fluid as the drilling fluid is pumped through the probe assembly (108). The sample size of drilling fluid taken by the AES meter (100) may be approximately 50 milliliters. However, one of ordinary skill in the art will appreciate that the sample size may vary based on, for example, the drilling fluid being tested, the area of the probe gap, etc. In one or more embodiments, the AES meter (100) may be located off-shore, at or near the location of the drilling fluids. The readings/data acquired by the AES meter (100) may then be transmitted over serial lines to a data acquisition system (not shown) which may be located off-shore or on-shore.

Those skilled in the art will appreciate that although the aforementioned discussion of FIG. 1 focuses on measuring the electrical stability of drilling fluid, the AES meter may be used to automatically measure other properties of drilling fluids that yield useful information about drilling fluid composition and stability. For example, changes in water content due to an influx from the formation or other source, water flow rates, and/or oil-to-water ratios of sampled drilling fluid may be measured using the AES meter. In addition, oil-wetting properties of the drilling fluid, drilling fluid conductivity and/or permittivity, and other properties may also be measured using the AES meter. To measure other properties of the drilling fluid, the electrical stability test procedure is modified to gather current and voltage data below the breakdown voltage discussed above.

Figure 3:
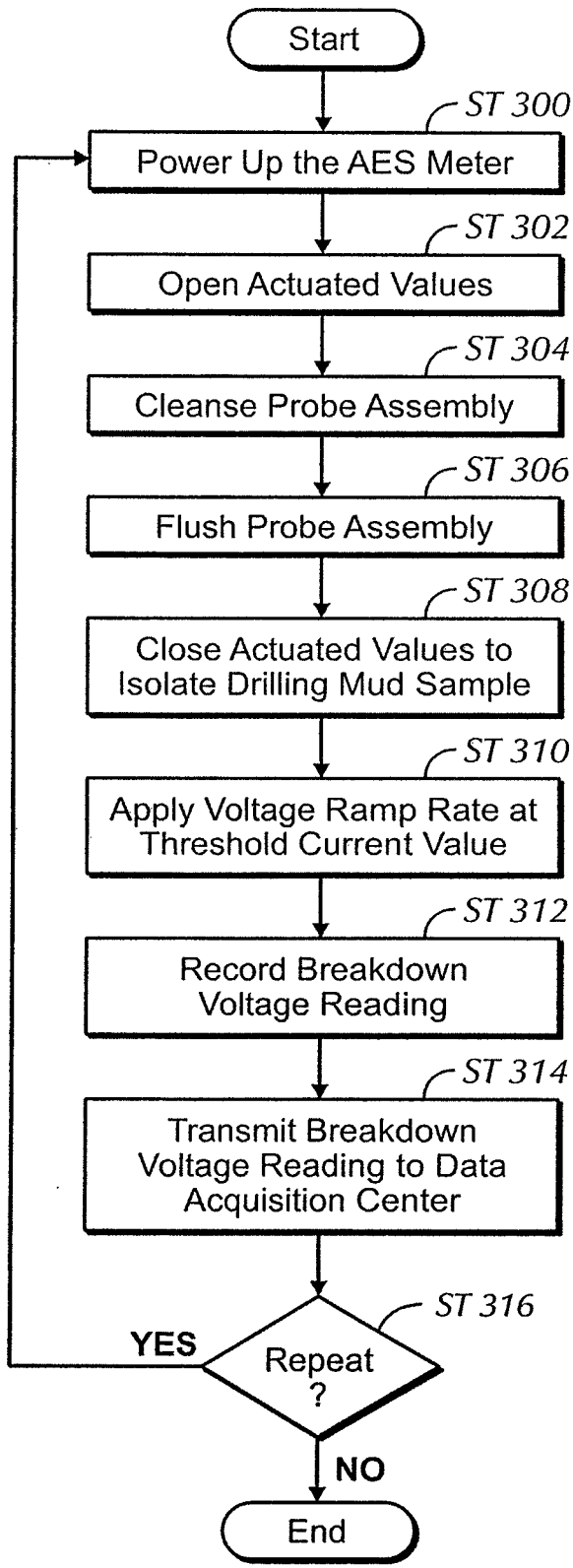
FIG. 3 shows a flow chart in accordance with embodiments disclosed herein.

FIG. 3 shows a flow chart in accordance with one or more embodiments of the invention. Initially, the AES meter is powered up in automatic mode (ST 300). After a short initialization delay, the inlet and outlet valves are opened to obtain a sampling of drilling fluid (ST 302). By opening the inlet and outlet actuated valves, drilling fluid is pumped through the probe assembly. Next, the probe gap is cleaned (ST 304). Cleansing of the probe gap is primarily performed to remove any previously tested drilling fluid, as well as to remove remnants of the short-circuiting bridge from the measurement chamber and the electrode surfaces. As mentioned above, various cleansing methods may be employed, such as the use of a wiper arm that moves in and out of the probe gap, a rapid flow of drilling fluid through the chamber, high-speed jetting of fluid through the chamber, etc. In one or more embodiments, if continuous drilling fluid sampling is employed, then drilling fluid coursing through the hose may be sufficient to clean the electrodes.

The probe assembly is subsequently flushed with drilling fluid (ST 306), and the inlet and outlet valves are closed to isolate the drilling fluid sample (ST 308). Trial and error may be used to determine the duration of the flush period. The probe assembly is flushed by pumping the drilling fluid through the hoses that go through the probe assembly for a fixed period. Flushing the probe assembly allows the drilling fluid sample previously tested to be removed from the cell where the probe is located and also allows for new drilling fluid to be deposited in the probe gap. In one or more embodiments of the invention, the drilling fluid is flushed out of the probe assembly using base oil and solvent degreaser, before storage or before initiating flushing with fresh drilling fluid. Closing the actuated valves stops the flow of drilling fluid and creates a quiescent period during which the voltage ramp may be executed. Those skilled in the art will appreciate that the AES meter may also employ an alternative continuous process for sampling and measuring the drilling fluid, in which case the electrode probe may be installed directly in the path of the drilling fluid pump that pumps drilling fluid through the probe assembly, such that the sample chamber (i.e., the probe assembly cell) becomes the line between the active system and the mud pump. In this case, the electrode probe is exposed to fresh drilling fluid continuously.

At this stage, the API standard electrical stability probe waveform is executed, the voltage between the electrodes of the probe is automatically ramped up according to the waveform when the threshold current value is reached (ST 310), and the electrical stability of the sample drilling fluid is measured (i.e., the breakdown voltage reading is taken and recorded) (ST 312). The breakdown voltage reading is then sent over serial lines to the data acquisition center (ST 314). The AES meter subsequently opens the actuated valves and allows the drilling fluid to flow continuously until it is time for the next measurement reading. Those skilled in the art will appreciate that the above steps may repeat (ST 316) for each measurement reading, as the AES meter is automated to cycle the above sequence of steps as desired.

Advantageously, embodiments disclosed herein provide an improved electrical stability meter for automatically measuring various properties of invert emulsion non-aqueous fluids, such as oil-based drilling fluids and synthetic-based drilling fluids. Particularly, embodiments provide an AES meter and method for using the AES meter to measure the electrical stability of such non-aqueous fluids. Using such measurements, trends over time of this drilling fluid property can be analyzed to obtain information of a fluid's emulsion stability and guide the treatment of the fluid. Further, the AES meter of the present invention is versatile in its application, as the waveforms and specifications (e.g., voltage ramp rates) used to measure the electrical stability and other properties of the drilling fluid may be changed via configuration files provided to the ECM. In addition, the geometry of the probe gap (e.g., a larger electrode area) may also be varied with use of the automated electrical stability test, which would result in a larger current and a larger breakdown voltage than described above.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

What is claimed:

1. A method comprising:
   obtaining a sample of a fluid, wherein the sample of the fluid is obtained by directing the fluid through an electrode probe assembly comprising a cell and an electrode probe and depositing the fluid in a probe gap between electrodes of the electrode probe, wherein the electrode probe is disposed in the cell;
   increasing a voltage to the electrodes of the electrode probe until a threshold current is obtained;
   recording a breakdown voltage at the threshold current value;
   using the breakdown voltage to compute a property of the sample of the fluid; and
   driving a wiper in and out of the probe gap to clean the electrode probe,
   wherein at least two of the obtaining a sample, increasing a voltage and driving the wiper are performed automatically by an electronic control module.

2. The method of claim 1, wherein obtaining a sample of fluid comprises opening at least one valve.

3. The method of claim 1, further comprising:
   isolating the sample of fluid.

4. The method of claim 1, wherein the fluid is an invert emulsion fluid.

5. The method of claim 1, further comprising ramping up the voltage using a software program that comprises a waveform specifying voltage ramp rates.

6. The method of claim 1, wherein the property of the sample comprises at least one selected from a group consisting of an oil-wetting property of the fluid, changes in water content of the fluid, an electrical stability of the fluid, a conductivity of the fluid, and a permittivity of the fluid.

7. The method of claim 1, further comprising:
   transmitting the breakdown voltage to a data acquisition center, wherein the data acquisition center is located at one selected from a group consisting of a remote location and a local rig location.

8. A meter comprising:
   an electronic control module configured to send a signal to obtain a sample of fluid;
   a probe assembly, operatively connected to the electronic control module, comprising a cell and an electrode probe disposed in the cell, wherein the electrode probe comprises at least two electrodes and a probe gap, and wherein the sample of fluid is pumped through the probe assembly and fills the probe gap and a voltage is ramped as the fluid is pumped through the probe assembly and fills the probe gap to obtain a breakdown voltage measurement that occurs at a threshold current value, and wherein the breakdown voltage measurement is used to automatically measure a property of the sample of the fluid;

a cleaning mechanism configured to periodically cleanse the probe gap as signaled by the electronic control module, wherein the cleaning mechanism is a wiper operatively connected to the probe assembly and configured to periodically move in and out of the probe gap to remove fluid from the at least two electrodes; and an actuated valve, wherein the electronic control module is configured to control at least two of the actuated valve, the cleaning mechanism, and the voltage.

9. The meter of claim 8, further comprising:
actuated valves controlled by the electronic control module configured to open and close, wherein the actuated valves open to allow the flow of fluid through the probe assembly.

10. The meter of claim 8, wherein the electronic control module is further configured to control the frequency of sampling of the fluid.

11. The meter of claim 8, further comprising:
a mud inlet hose for sending the fluid into the probe assembly; and
a mud outlet hose for sending the fluid out of the probe assembly, wherein the mud inlet hose and the mud outlet hose are both operatively connected to the probe assembly.

12. The meter of claim 8, wherein the electronic control module receives a configuration file comprising a waveform specifying voltage ramp rates, wherein the configuration file is stored on a computer readable medium operatively connected to the electronic control module.

13. The meter of claim 12, wherein the configuration file is used to define a voltage ramping procedure and a sample frequency of breakdown voltage measurements.

14. The meter of claim 8, wherein the property of fluid comprises at least one selected from a group consisting of an oil-wetting property of the fluid, changes in water content of the fluid, an electrical stability of the fluid, a conductivity of the fluid, and a permittivity of the fluid.

15. The meter of claim 8, wherein the electronic control module automatically determines when to clean the probe gap.

16. A meter comprising:
an electronic control module configured to send a signal to obtain a sample of fluid;
a probe assembly, operatively connected to the electronic control module, comprising a cell and an electrode probe disposed in the cell, wherein the electrode probe comprises at least two electrodes and a probe gap, and wherein the sample of fluid is pumped through the probe assembly and fills the probe gap and a voltage is ramped as the fluid is pumped through the probe assembly and fills the probe gap to obtain a breakdown voltage measurement that occurs at a threshold current value, and wherein the breakdown voltage measurement is used to automatically measure a property of the sample of the fluid;
a cleaning mechanism configured to periodically cleanse the probe gap as signaled by the electronic control module; and
an actuated valve,
wherein the electronic control module is configured to control at least two of the actuated valve, the cleaning mechanism, and the voltage, and
wherein the cleaning mechanism uses ultrasound techniques to remove previously tested fluid from the probe gap.

* * * * *